Figure 1:
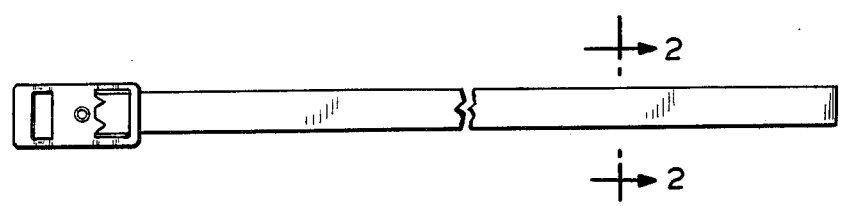

United States Patent [19]

Ford

[11] 4,159,314
[45] Jun. 26, 1979

[54] INSECT REPELLENT ANIMAL COLLAR

[75] Inventor: Stuart Ford, Manakin, Va.

[73] Assignee: Stuart Ford Incorporated, Richmond, Va.

[21] Appl. No.: 788,609

[22] Filed: Apr. 18, 1977

[51] Int. Cl.² .................... A01K 27/00; A01K 29/00; A01M 1/20
[52] U.S. Cl. .................... 424/14; 119/156; 424/16; 424/28
[58] Field of Search ............ 424/14, 16, 28; 119/156

[56] References Cited

U.S. PATENT DOCUMENTS 3,904,746  9/1975  Aries ..................... 424/28

OTHER PUBLICATIONS

Hocking, "A Dictionary of Terms in Pharmacognosy", C. C. Thomas, Publisher, Springfield, Ill. (1955), p. 228 Thuja, (T. Occidentals), Volatile Oil (VO) Insect/Repellant, p. 45 Cedar, Cedarleaf Oil, etc., p. 117 Junipor, Juniporis, Cedarwood Oil, etc.
Chem. Abstracts 82, #81691u (1975) of Japan Kokai 74 85230, 21 Dec. 1972, Thujaplicin (Hinokitiol) Insecticide; Protects Leather and Textiles against Insects.
Chem. Abstracts, 81 #34595k (1974) of Japan 73 33,375, 13 Oct. 1973, Thujaplicin (Hinokitiol) Acaricide Effective for Control of Mites.

Primary Examiner—Shep K. Rose
Attorney, Agent, or Firm—Stephen E. Feldman; Marvin Feldman

[57] ABSTRACT

An insect repellent animal collar is disclosed wherein a strip of flexible polymeric material adapted to be worn on the neck of the animal is impregnated with a thujane derivative such as thujic acid, thujic ester, thujone and a thujaplicin, or a mixture thereof. The thujone derivative is released through the porous structure of the polymeric material.

10 Claims, 2 Drawing Figures

INSECT REPELLENT ANIMAL COLLAR

This invention relates to the control of insects, particularly fleas, on animals such as cats and dogs, by use of a specific insect repellent composition in a collar to be worn by the animal.

Heretofore, pet collars comprised of a PVC resin having a dispersion of the insecticide dimethyl 2,2-dichlorovinyl phosphate commonly known as DDVP or by its trademark Vapona, have been widely used for the purpose of controlling fleas on dogs and cats. DDVP has been reported to have an objectionable depressing effect on the plasma and red cell cholineserase which is particularly acute at high concentrations which are produced during the first few days after a collar has first been applied to the neck of the animal. In addition, local skin irritation has occasionally occurred at the site of the collar, especially when a new collar is first placed on the animal, notwithstanding the smooth surface of the collar. This is believed due to the fact that liberation of DDVP from presently available DDVP collars and tags is not at a uniform rate, bur rather there is a high liberation rate of DDVP gas during the first few days after activation, i.e., removal of the collar from the packing and placing it on the neck of the animal. Moreover, the aforementioned initial high liberation rate represents an unduly rapid loss of insecticide and creates an upper limit on the period that DDVP is liberated at a rate sufficient to effectively control fleas.

In Greenberg, U.S. Pat. No. 3,918,407, granted Nov. 11, 1975 there is disclosed a proposed substitute for DDVP, namely dimethyl, 1,2-dibromo-2,2 dichloroethyl phosphate, commonly known as naled. Naled like DDVP is considered toxic, but Greenberg sought to provide controlled limited release of the naled.

Various prior art references, namely Bright, U.S. Pat. No. 275,352, granted Apr. 10, 1883; Cardogan, U.S. Pat. No. 824,409, granted June 26, 1906; Williamson, U.S. Pat. No. 1,720,587, granted Mar. 8, 1927; and Drushel, U.S. Pat. No. 1,630,836 granted May 31, 1927, disclose medicinal compounds and insecticides wherein a component material is cedar oil.

Wiesmann, U.S. Pat. No. 3,213,830, granted Oct. 26, 1965 discloses a neck oiler for cattle for application to infected neck regions of cattle.

Now there is found by the present invention that nontoxic cedar oil and more specifically certain components thereof may be incorporated into a polymeric strip to serve as a controlled release insect repellent animal collar.

It is a principal object of this invention therefore to provide a substitute for the DDVP and 1,2dibromo-2,2 dichloroethyl phosphate heretofore used in pet collar applications.

It is another object of this invention to provide a non-toxic flea repellent.

Another object of this invention is to provide a pet collar as aforesaid which is readily fabricated, and of relatively inexpensive cost, and yet safe and practical in use.

Figure 2:

These and other objects of the invention will become more fully apparent from the claims, and from the description as it proceeds in connection with the appended drawings wherein:

FIG. 1 is a plan view of a representative pet collar embodying the present invention; and FIG. 2 is a view of the collar in cross section taken along lines 2—2 of FIG. 1.

Broadly stated the insect repellent collar of this present invention comprises:

a strip of flexible polymeric material adapted to encircle the neck of the animal with means to fasten the strip to prevent loss of the collar from the neck of the animal, and an insect repellent composition comprising a thujane derivative, said composition being carried by the strip.

By the term "thujane derivative" it is meant a compound being derived from the bicyclic terpene, thujane of the following structure:

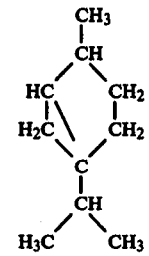

Suitable thujane derivaties useful pursuant to the present invention include the thujane esters, such as the alkyl esters (e.g. methyl thujate, ethyl thujate) and the like; thujic acid; thujic ketones (e.g. thujone); and thujaplicins (e.g. beta-thujaplicinol, gamma-thujaplicin, beta-thujaplicin, alphathujaplicin, beta-dolabrin, and the like). It is also within the contemplation of this invention, that the term thujone derivatives include the thujaplicin derivatives as well. Suitable thujaplicin derivatives includes, thujaplicatin esters (e.g. thujaplication methyl ester), nezukone (a tropone) and the like.

One primary source of the thujane derivatives useful in the present invention is in the oil extractives of cedar wood. The following table shows an analysis of the thujane derivatives in cedar oil extract and in the cedar wood itself.

| Component | % of Oil | % of Wood |
|---|---|---|
| Methyl thujate and other neutrals | 21.1 | 0.17 |
| Thujic acid | 10.4 | .08 |
| Thujaplicins | 68.5 | .56 |
| β-thujaplicinol | 8.0 | .07 |
| γ-thujaplicin | 24.0 | .20 |
| β-thujaplicin | 35.0 | .30 |
| α-thujaplicin | 1.0 | .01 |
| β-dolabrin | 0.04 | .0003 |

One thujane derivate may be present in the collar in amounts of from about 10 to 50% by weight of the plastic substrate, although more or less may be incorporated in as well.

Further discussion of the well-known thujane derivatives is made by reference to the text, Perfume and Flavor Chemicals, S. Arctander, vol. II, secs. 2940–41, priv. publ. (1969)

Referring now to the drawings, FIGS. 1 and 2 show a typical collar adapted for pets such as dogs or cats. The components making up a satisfactory thujone derivative containing pet collar include a synthetic resin that is sufficiently pliable or flexible to be encircled around the animal's neck and has strength sufficient to remain on the animal throughout a period of at least a few months or the period during which the thujane derivatives are released in amounts effective to control fleas.

The collar constitutes a band or strip of a PVC-thujane derivative combination with the concentration of PVC sufficiently large to give the collar physical properties such as strength, flexibility, and freedom from tackiness to make it suitable for use as a collar for the animal. Normally, the cross-sectional dimensions of the collar vary from about one-fourth to five-eighth inch in width, and from about three thirty-seconds to three-sixteenths inch in thickness. For collars of the present invention employing the PVC-thujane derivative combination, the preferred dimensions are three-eigths in width and one-eigth inch in thickness, and the cross section is as illustraded in FIG. 2.

The collars are made of sufficient length to encircle the neck of the largest dog or cat to be encountered, and for smaller animals, the end of the collar may be cut off to reduce the size of the collar to correspond with the size of the animal. With the PVC-thujane derivative combination and dimensions as given above, the perimeter of the collar is about one inch and the mass of the collar is about one gram per lineal inch. By use of a clasp having a friction grip, the collar can be adjustably placed on the animal without the need for holes.

From the standpoint of toxicity, there is no concern insofar as the thujane derivatives are not toxic to the animals, and the cedar oil extracts may themselves be incorporated in the PVC substrate.

The thujane derivatives exist within the matrix of the resin of the collar as separate entities to be gradually released upon migration to the surface where they are dispersed to the immediate environment of the collar. Most of the thujane derivatives, particularly the esters escape as vapor. In order for the thujane derivatives to escape, they move outward through the interstices or pores of the resin to the porous surface openings. The internal porosity, texture and surface porosity of the resin must be sufficiently coordinated to allow a sufficient release from the resin to effectively control fleas for a period of several days.

Heretofore there was concern about DDVP or dimethyl, 1,2-dibromo-2,2 dichloroethyl phosphate concentrating in droplets on the collar and because of the concentration having a toxic effect on the animal. No such concern is believed necessary in using the cedar oil extracted thujane derivatives of the present invention. And the porous structure of the plastic collar may permit droplets to be formed.

The various known synthetic resins which can be used for the pet collar substrate include materials such as polyethylene, polyproplyene, copolymers of ethylene and propylene, nylon, cellophane, polyacrylates, such as polymers and copolymers of methylacrylate, ethylacrylate, methymethacrylate and ethylmethacrylate; polymers of vinyl compounds, such as polystyrene, polymerized divinylbenzene; polyvinyl halogenides, such as polyvinylchloride; polyvinylacetals, such as polyvinylbutyral; polyvinylidene compounds, such as polyvinylidenechloride; polyvinylacetate; ethyl-vinylacetate copolymers; copolymers of vinylchloride and vinylacetate; polyurethanes, polyaldehydes; and thermoplastics other than as above as well.

It is also within the contemplation of this invention to incorporate porosity control additives with the resin substrate structure. The main function of the additive is to provide a surface porosity by forming pores in the resin substrate. Suitable porosity control additives include chloroacetaldehyde, dichloroacetaldehyde, chloral, bromoacetaldehyde, dibromoacetaldehyde, bromal, bromodichloroacetaldehyde, chlorodibromoacetaldehyde, bromochloroacetaldehyde and 2-bromopropanol.

In addition, various inorganic and organic diluents may be added to the thujane derivatives to control the flow release and vapor pressure release. Suitable diluents include hexane cyclohexhane, xylene, benzene, terpenes, and the like.

The collar in accordance with the present invention is produced to have a porous outer surface to not only release thujane derivatives at a rate higher than otherwise possible and in a greater gross amount, but also to release the thujane derivatives at a rate effective to control fleas for a substantially longer period than otherwise possible.

The present invention may be embodied in other specific forms without departing from the spirit or essential characteristics thereof. The presently disclosed embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A flea repellent dog or cat collar comprising:
   a strip of flexible thermoplastic material adapted to encircle the neck of the dog or cat with means to fasten the strip to prevent loss of the collar from the neck, said thermoplastic being formed with a plurality of pores and being impregnated with a thujane derivative thereby providing an effective flea repellent collar.

2. The collar of claim 1, wherein the thujane derivative is one selected from the group consisting of a thujic acid, a thujic ester, a thujone, and a thujaplicin, or a mixture of the above.

3. The collar of claim 1, wherein the thermoplastic material comprises polyvinyl chloride.

4. The collar of claim 2, wherein the thujic ester is an alkyl thujate.

5. The collar of claim 1, wherein the pores are sufficient to permit droplets of the thujane derivative to form on the collar.

6. The collar of claim 2, wherein the thujaplicin comprises a thujaplicin derivative.

7. The collar of claim 1, where the thujane derivative is present in an amount of from 10 to about 50 percent by weight of the polymeric material.

8. The collar of claim 1, wherein the thujane derivative is an alkyl ester, and wherein the ester forms droplets within the pore structure and vaporizes from the pore structure.

9. The collar of claim 8, wherein the alkyl ester is methyl thujate, ethyl thujate or a mixture thereof.

10. The collar of claim 8, wherein the thujane derivative is derived from cedar oil.

* * * * *